United States Patent [19]

Schmidtberger

[11] 4,118,379

[45] Oct. 3, 1978

[54] AMIDATED IMMUNE GLOBULINS AND PROCESS FOR PREPARING THEM

[75] Inventor: Rudolf Schmidtberger, Marburg-Marbach, Fed. Rep. of Germany

[73] Assignee: Behringwerke Aktiengesellschaft, Marburg an der Lahn, Fed. Rep. of Germany

[21] Appl. No.: 770,181

[22] Filed: Feb. 18, 1977

Related U.S. Application Data

[63] Continuation of Ser. No. 610,458, Sep. 4, 1975, abandoned.

[30] Foreign Application Priority Data

Sep. 6, 1974 [DE] Fed. Rep. of Germany ....... 2442655

[51] Int. Cl.$^2$ ................................................ A23J 1/06
[52] U.S. Cl. ................................. 260/112 B; 424/101
[58] Field of Search ..................... 260/112 B; 424/101

[56] References Cited

U.S. PATENT DOCUMENTS 3,857,931  12/1974  Hager ............................... 260/112 B

*Primary Examiner*—Walter C. Danison
*Attorney, Agent, or Firm*—Curtis, Morris & Safford

[57] ABSTRACT

The invention relates to modified immune globulins, a process for preparing them by treating immune globulins in a slightly acidic to neutral solution with a molar excess of a primary amine and a carbodiimide or salts thereof and pharmaceutical compositions containing modified immune globulins.

17 Claims, No Drawings

AMIDATED IMMUNE GLOBULINS AND PROCESS FOR PREPARING THEM

This is a continuation of application Ser. No. 610,458, filed Sept. 4, 1975, now abandoned.

The invention relates to modified immune globulins, a process for preparing them and pharmaceutical compositions containing modified immune globulins. It especially concerns chemically modified immune globulins which may be administered via the intravenous route.

Immune globulins prepared by fractionation from serum, especially from human serum, have the essential property to act as antibodies against antigens.

Immune globulin compositions have hitherto proved suitable only for intramuscular administration. In the case of intravenous administration, the recipients have shown a more or less marked reaction with anaphylactoidal effects.

It is supposed that these secondary reactions are due to the fact that the serum complement is bound by the immune globulin administered. On the other hand an intraveneous immune globulin composition is desired since it deploys it activity faster in the organism.

It has been attempted several times to modify the immune globulins in such as way as to maintain their activity as antibodies and to reduce the degree of complement binding to such an extent that the modified immune globulins can be used for intravenous administration. For example, immune globulin molecules may be modified by enzymatic degradation, so that the linking points for the complement are split off, but the reset of the molecules is capable of binding antigens. Such a composition is administered intraveneously with good success.

The reaction of immune globulins with alkylating and acylating agents also leads to an immune globulin suitable for intravenous administration. The reduction of the complement binding of immune globulins may also be obtained by N-alkylation and benzylation.

Furthermore, a process is known according to which immune globulins are partly split by reduction of intramolecular disulfide bonds and the sulfhydrils formed are subsequently alkylated. In this process the original size of the molecule is maintained.

These processes are essentially based on the modification of the free amino groups or disulfide bonds of the immune globulin molecules.

Though these processes lead to products having rather satisfying properties, problems persist to which improved solutions should be found, especially because the physical and chemical properties of the molecules are considerably modified by the processes described.

It has now been found that immune globulins in which some carboxyl groups have been modified considerably change their binding behavior with regard to complement without losing their efficiency as antibodies. Such modified immune globulins, which bind complement to a smaller extent or in a not detectable degree, are suitable as medicaments for intravenous administration.

Thus, the objects of the invention are amidated immune globulins and futhermore a process for preparing such amidated immune globulins, wherein immune globulins are reacted with a molar excess of a primary monoamine and a carbodiimide in a slightly acidic to neutral aqueous solution. The molar ratio of the amine to immune globulins expediently amounts to at least 50:1 and the ratio of carbodiimide to immune globulins to at least 1:1.

As starting material for the reaction of the invention there are used immune globulin fractions obtained from sera, plasmea or other body liquids or organ extracts. Especially the fractions enriched with regard to immune globulin are used. A preferred method for preparing them is, for example, the method according to Levy and Sober via chromatography on DEAE cellulose. Naturally, the pure immune globulins may also be amidated according to the invention. However, in practice the 100% pure immune globulins do not play an important part for the time being, due to the expensive processes of purification.

It has appeared that the complement bond of the immune globulins provides particularly low values if the ratio of carbodiimide to immune globulins is 5:1 to 20:1.

As amines in the sense of the invention, all primary monoamines, i.e. compounds of the general formula $$R - NH_2,$$

wherein R is a radical which according to known conceptions does not represent any marked antigen motive in immunology, are suitable.

Examples of suitable amines are above all aliphatic amines, methyl amine, ethyl amine and higher aliphatic amines, especially those having up to 10 carbon atoms. In the slightly acidic aqueous solutions used, the amines are generally present as the corresponding ammonium cations. According to the invention those amines are preferred which carry further functional groups, especially hydrophilic groups such as hydroxy or acetal. Examples of such amines are ethanol amine, trishydroxymethylamino-methane or glucosamine, which have a favorable influence on the solubility of the reaction product in a physiologically compatible aqueous medium.

Since the process is carried out under conditions under which the antibody activity of the immune globulin must not be adversely affected, it is expedient to carry out the reaction in a known manner in the presence of a carbodiimide as in activator. As the carbodiimide there are suitable all representatives of this class of compounds which are capable of having an activating effect on the formation of peptide bonds. Examples for such carbodiimides are 1-ethyl-3-(3-dimethylaminopropyl)-carbodiimide-hydrochloride (EDC) or 1-cyclohexyl-3-(2-morpholinoethyl)-carbodiimide-metho-p-toluene-sulfonate (CMC). In the same way as the amines, the carbodiimides are present as salts in the slightly acidic aqueous solutions used. The carbodiimides are generally used as salts since they are more stable and easier to handle in this form. On principle, the free carbodiimides may also be used; when being dissolved in the aqueous solution they pass to the salt form.

The testing of the complement bond may be carried out according to A. Nowotny, Basic Exercises in Immunochemistry, page 160 et seq. (1969).

The process of the invention for preparing amidated immune globulins may also be carried out with immune globulins in which disulfide groups present are reduced to sulfhydril groups. The products amidated after the reduction have the same advantageous properties.

For the reduction of disulfide bonds it is, for example, particularly advantageous to use dithiothretol or dithioerythritol. The disulfide bonds may also be reduced according to a known process with reducing agents such as 2-mercapto-ethanol or mercaptoethyl amine while using high concentrations of the reducing agent.

The reducing agents described by Cleland having the following formulae:

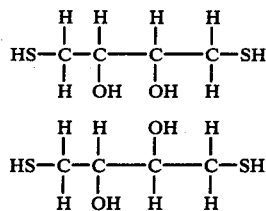

may be used for the reduction of the immune globulins.

Amidated immune globulins having a sufficient reduction of the complement bond may be administered by the intravenous route. They may be treated with physiologically compatible solvents to obtain the corresponding compositions. Medicaments containing amidated immune globulins may be made available in a liquid or freeze-dried form.

The following Examples illustrate the invention.

EXAMPLE 1

Preparation of the starting material.

22.1 Liters of human serum obtained from spontaneously coagulated blood were passed for salt formation over a column equilibrated with 0.0175 molar sodium phosphate, pH 6.4, filled with Sephadex G-25 ®"medium" (registered trade mark of Messr. Pharmacia for cross-linked dextran). With a passage photometer, the absorption was measured in the column eluate at 280 nm. The first peak formed by the serum proteins was collected separately from the following low molecular weight portions and passed over a column, rinsed with the above-mentioned phosphate buffer, of 15 kg of DEAE — cellulose with 1 mol equivalent/g of exchanger capacity. The column was rinsed afterwards with 1.5 column volumes of buffer. The immune globulins in the passage of the column were precipitated by addition of solid ammonium sulfate up to a concentration of 2.2 moles per liter. Most part of the supernatant liquid was siphoned off after standing for 24 hours; the rest was eliminated by centrifugation at 5200 g. The residue of the centrifuge was freed from ammonium sulfate by dialysis against 0.1 molar NaCl solution. The volume of the dialysed immune globulin solution was filled up with a NaCl solution to 2000 ml. It contained 155 g of protein on the whole.

Amidation of the immune globulin.

1000 ml of the immune globulin solution obtained according to the process described above were dialysed for 24 hours while stirring against 1000 ml of 1 molar tris-hysroxymethylaminomethane-("tris")-HCl buffer, pH 5.4, transferred to a glass vessel and mixed while stirring with 0.96 g 1-ethyl-3-(3-dimethylaminopropyl)-carboxydiimide.HCl. The batch was stirred for 2 hours at room temperature.

The immune globulin amidated with tris-hydroxymethylamino-methane was passed over a column containing 8 liters of Sephadex G-25 ® which had been previously rinsed with a solution of 0.15 molar NaCl and 0.3 molar glycine having a pH value of 7.3. The optical density of the column eluate was measured at 280 nm with a passage photometer. The portion of the eluate containing the amidated immune globulin was combined and concentrated with an ultra filter to a content of protein of 5%.

The following Table shows a comparison of starting immune globulin to amidated immune globulin with regard to complement bond and antibody activity:

TABLE 1

|  | Complement bond[1] | German measles titer | Antibody specifity | |
|---|---|---|---|---|
|  |  |  | diphtheritis IU / ml | tetanus IU / ml |
| starting immune globulin | 22% | 1:1024 | >0.5 <1.0 | >1 <2 |
| amidated immune globulin | 0% | 1:1024 | >0.5 <1.0 | >1 <2 |

[1]the evaluation of the complement bond was effected according to NOWTNY, A., Basic Exercises in Immunochemistry; Springer Verlag, 1969, page 160.

EXAMPLE 2

1000 ml of immune globulin solution obtained according to Example 1, containing 75.5 g of protein, were mixed with 890 ml of a solution containing 52.2 g of glucosamine.HCl and the pH value was adjusted to 6.0 with 2 molar NaOH. With stirring, 2.06 g of 1-cyclohexyl-3-(2-morpholinyl-4-ethyl)carbodiimidemetho-p-toluene sulfonate were added to the solution and stirring of the batch was continued. The reaction temperature was 25° C. The transfer of the amidated immune globulin into a solution containing 0.15 mole per liter NaCl and 0.3 mole per liter of glycine of pH 7.3 was carried out in the manner described in Example 1, but with a column containing 10 liters of Sephadex G-25 ®. The concentration to 5% of protein was also effected as described in Example 1. The results of the evaluation of the amidated immune globulin obtained according to Example 2 are compared with those of the starting globulin in Table 2.

TABLE 2

|  | Complement bond | German measles, titer | Antibody specifity | |
|---|---|---|---|---|
|  |  |  | diphtheritis IU / ml | tetanus IU / ml |
| starting immune globulin | 22% | 1:1024 | >0.5 <1.0 | >1 <2 |
| amidated immune globulin | 1.5% | 1:1024 | >0.5 <1.0 | >1 <2 |

EXAMPLE 3

Reduction and amidation of the immune globulins.

The amidation of the immune globulins described in Example 1 and 2 may be carried out in the same way with reduced immune globulins. the reduction was carried out as follows:

A solution of 3.3 g of immune globulin in 330 ml of 0.15 molar NaCl solution was adjusted to pH 8.2 with tris(hydroxymethyl)-aminomethane (Tris). To the immune globuline solution, 15.3 mg of dithioerythritol (DTE) dissolved in 2 ml of water were added. After 60 minutes, 20 ml of a tris-HCl solution containing 5 g of Tris, of pH 1.0, were added while stirring. The pH value of the mixture was adjusted to 5.0 with HCl and amidated as described in Example 1 after addition of 82.2 mg of N-ethyl-N'-(3-dimethylaminopropyl)-carbodiimide.HCl.

The reduction of the immune globulins may be carried out with dithiothreitol (DTT), instead of dithioerythritol, under the same test conditions.

What is claimed is:

1. The method of making water-soluble amidated immune globulins which comprises reacting immune globulins with a molar excess of a water-soluble primary monoamine and a water-soluble carbodiimide or a salt thereof in a slightly acidic to neutral aqueous solution.

2. A method as in claim 1 wherein the molar ratio of amine to immune globulines is at least 50:1 and the ratio of carbodiimide to immune globulines is at least 1:1.

3. A method as in claim 1 wherein the molar ratio of carbodiimide to immune globulines is from 5:1 to 20:1.

4. A method as in claim 1 wherein said amine is an aliphatic monoamine having 1 to 10 carbon atoms.

5. A method as in claim 4 wherein said aliphatic monoamine is hydroxy-substituted.

6. A method as in claim 4 wherein said aliphatic monomine is acetal-substituted.

7. A method as in claim 1 wherein said amine is ethanol amine, trishydroxymethylaminomethane, or glucosamine.

8. A method as in claim 1 wherein said carbodiimide is 1-ethyl-3-(3-dimethylaminopropyl)-carbodiimide hydrochloride or 1-cyclohexyl-3-(2-morpholino-ethyl)-carbodiimide-metho-p-toluene sulfonate.

9. A method as in claim 1 wherein the reaction is carried out at a pH-value of 3 to 7.

10. A method as in claim 1 wherein the reaction is carried out at a temperature from 5° to 50° C.

11. A method as in claim 1 wherein said immune globulins are human immune globulins.

12. A method as in claim 1 wherein said immune globulins comprise at least one disulfide bond converted into two sulfhydril groups with the aid of a reducing agent.

13. A method as in claim 12 wherein the conversion of the disulfide bond into sulfhydril groups is carried out with a reducing agent at a slightly alkaline pH-value.

14. A method as in claim 13 wherein the concentration of the reducing agent is 0.01 mol/l and the molar ratio of protein to reducing agent is 2.5:1 to 50:1.

15. A method as in claim 12 wherein said reducing agent is dithioerythritol or dithiothreitol.

16. Water-soluble amidated immune globulins prepared by the method of claim 1.

17. Water-soluble amidated immune globulins prepared by the method of claim 12.

* * * * *